US009443304B2

(12) United States Patent
Damkat

(10) Patent No.: US 9,443,304 B2
(45) Date of Patent: Sep. 13, 2016

(54) DEVICE AND METHOD FOR EXTRACTING INFORMATION FROM REMOTELY DETECTED CHARACTERISTIC SIGNALS

(71) Applicant: KONINKLIJKE PHILIPS N.V., Eindhoven (NL)

(72) Inventor: Chris Damkat, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 12 days.

(21) Appl. No.: 14/398,265

(22) PCT Filed: Apr. 19, 2013

(86) PCT No.: PCT/IB2013/053112
§ 371 (c)(1),
(2) Date: Oct. 31, 2014

(87) PCT Pub. No.: WO2013/164724
PCT Pub. Date: Nov. 7, 2013

(65) Prior Publication Data
US 2015/0125051 A1 May 7, 2015

Related U.S. Application Data

(60) Provisional application No. 61/640,767, filed on May 1, 2012.

(51) Int. Cl.
*G06K 9/00* (2006.01)
*G06T 7/00* (2006.01)
(Continued)

(52) U.S. Cl.
CPC ........... *G06T 7/0016* (2013.01); *A61B 5/0205* (2013.01); *G06T 7/20* (2013.01);
(Continued)

(58) Field of Classification Search
CPC ........... G06T 7/20; G06T 2207/20068; G06T 2207/30076; G06T 2207/30196; G06T 2207/20201; G06T 7/0016; G06T 2207/10016; G06T 2207/20182; A61B 5/0205; A61B 5/0816; A61B 5/14551; A61B 5/024
USPC ......................................... 382/128
See application file for complete search history.

(56) References Cited

U.S. PATENT DOCUMENTS 9,089,308 B2 * 7/2015 Canstein et al.
2008/0045847 A1 2/2008 Farag
(Continued)

FOREIGN PATENT DOCUMENTS

IN WO 2011/161307 A1 * 12/2011 ............... G06K 9/00
NL WO 2011/042858 A1 * 4/2011 ............... G06K 9/00
(Continued)

OTHER PUBLICATIONS

Yu Sun et al.,"Motion-Compensated Noncontact Imaging Photoplethysmography to Monitor Cardiorespiratory Status During Exercise" Journal of Biomedical Optics, vol. 16, No. 7, Jan. 1, 2011, pp 077010, XP055017559.*
(Continued)

*Primary Examiner* — Gregory F Cunningham
(74) *Attorney, Agent, or Firm* — Larry Liberchuk

(57) ABSTRACT

The present invention relates to a device and a method for extracting information from remotely detected characteristic signals. A data stream (24) derivable from electromagnetic radiation (14) emitted or reflected by an object (12) is received. The data stream (24) comprises a sequence of frames (66, 70, 92, 94; 108, 110, 112, 122, 124; 164, 66, 168), at least some of the frames comprise a frame section (68, 72; 174, 180, 186) 5 representative of a region of interest (56) attributable to the object (12). The region of interest (56) exhibits a continuous or discrete characteristic signal (136; 192) including physiological information (200) indicative of at least one at least partially periodic vital signal (20; 208). The sequence of frames (66, 70, 92, 94; 108, 110, 112, 122, 124; 164, 166, 168) further comprises a disturbing signal portion at least partially indicative of undesired object motion. 10 The characteristic signal (136; 192) can be stabilized by deriving a derivative signal form (78, 88, 98, 100, 102; 172, 176) from at least some frames of said sequence of frames (66, 70, 92, 94; 108, 110, 112, 122, 124; 164, 166, 168) through a dimensional reduction. A positional shift (74, 178) of a present derivative signal form (88, 98, 100, 102; 176) relative to a previous derivative signal form (78, 172) can be estimated. A present frame section (72; 180, 186) can be determined under consideration of the estimated positional shift (74, 178). Hence, the region of interest (56) can be tracked for at least partially compensating undesired object motion. Consequently, the disturbing signal portion can be at least partially compensated. The characteristic signal (136; 192) can be extracted from the sequence of frames (66, 70, 92, 94; 108, 110, 112, 122, 124; 164, 166, 168) under consideration of a sequence of determined frame sections (68, 72; 174, 180, 186).

12 Claims, 7 Drawing Sheets

(51) Int. Cl.
*G06T 7/20* (2006.01)
*A61B 5/0205* (2006.01)
*A61B 5/024* (2006.01)
*A61B 5/08* (2006.01)
*A61B 5/1455* (2006.01)

(52) U.S. Cl.
CPC ............ *A61B 5/024* (2013.01); *A61B 5/0816* (2013.01); *A61B 5/14551* (2013.01); *G06T 2207/10016* (2013.01); *G06T 2207/20068* (2013.01); *G06T 2207/20182* (2013.01); *G06T 2207/20201* (2013.01); *G06T 2207/30076* (2013.01); *G06T 2207/30196* (2013.01)

(56) References Cited

U.S. PATENT DOCUMENTS

| | | | | |
|---|---|---|---|---|
| 2009/0141124 | A1* | 6/2009 | Liu et al. | 348/65 |
| 2010/0013919 | A1* | 1/2010 | Lin et al. | 348/143 |
| 2011/0251493 | A1 | 10/2011 | Poh | |

FOREIGN PATENT DOCUMENTS

| | | |
|---|---|---|
| WO | W02005008597 A2 | 1/2005 |
| WO | W02011021128 A2 | 2/2011 |
| WO | W02011042858 A1 | 4/2011 |
| WO | W02011161307 A1 | 12/2011 |

OTHER PUBLICATIONS

Stefano Alliney et al., "Digital Image Registration Using Projections", Transactions on Pattern Analysis and Machine Intelligence, IEEE, Piscataway, USA, vol. 30, No. 2, Mar. 1, 1986, pp. 222-233, XP011242921.*

Verkruysse W. et al., "Remote Plethysmographic Imaging Using Ambient Light", Optics Express, Optical Society of America, Washington, D.C., USA, vol. 16, No. 26, 2008, pp. 21434-21445.

Poh M-Z et al., "Non-Contact, Automated Cardiac Pulse Measurements Using Video Imaging and Blind Source Separation", May 10, 2010, vol. 18, No. 10, OPTICS EXPRESS 10762, Optical Society of America.

Ratakonda K., "Real-Time Digital Video Stabilization for Multi-Media Applications", Circuits and Systems, ISCAS '98, Proceedings of the 1998 IEEE International Symposium on Circuit and Systems, vol. 4, pp. 69-72, May 1998.

Mateos, G.G., "Refining Face Tracking with Integral Projections", Dept. de Informática y Sistemas University of Murcia —Spain, AVBPA 2003, Guildford Jun. 2003.

* cited by examiner

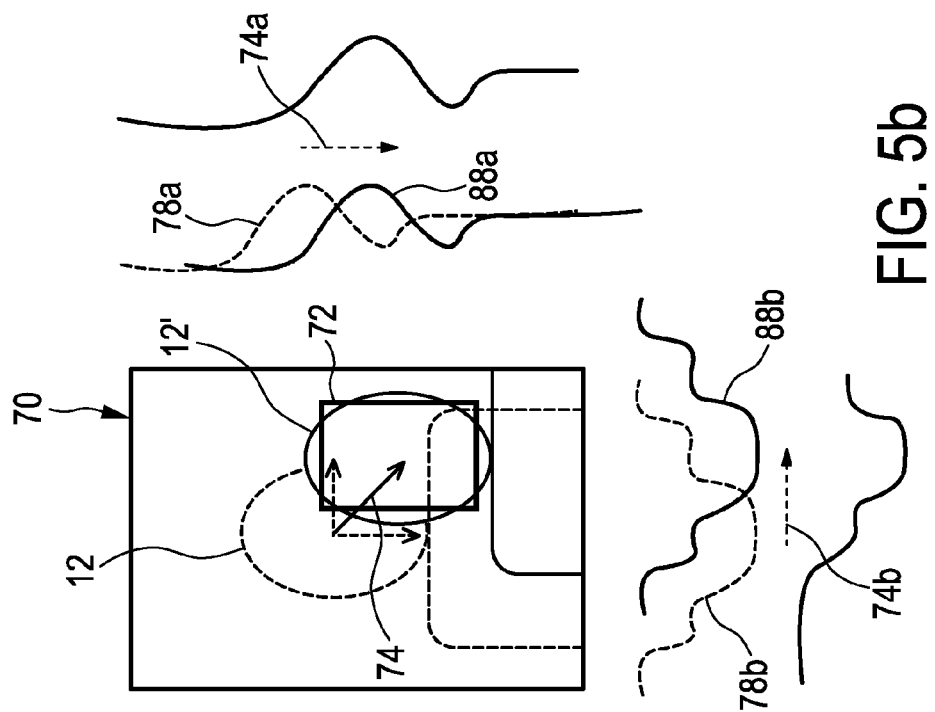
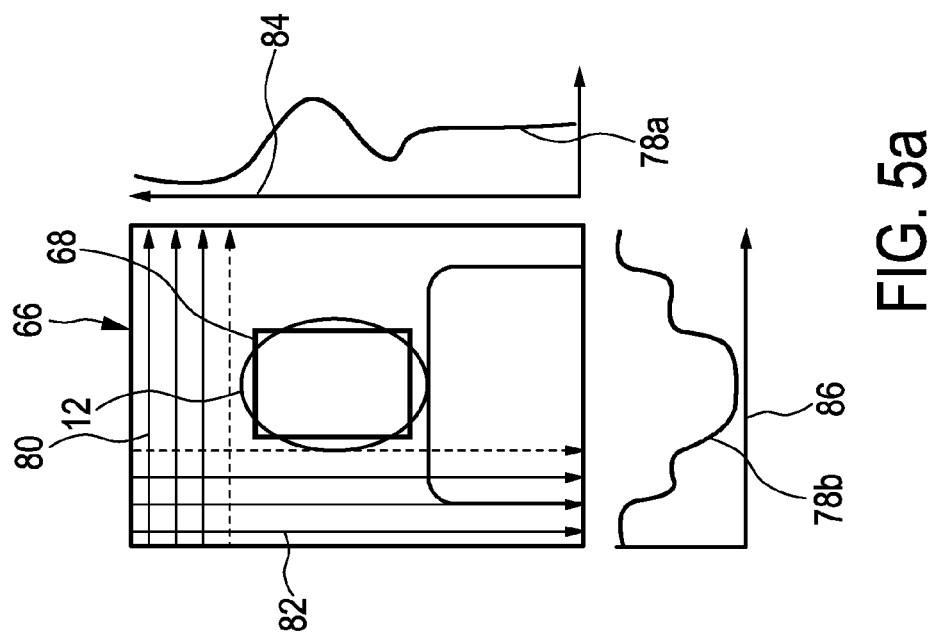

US 9,443,304 B2

DEVICE AND METHOD FOR EXTRACTING INFORMATION FROM REMOTELY DETECTED CHARACTERISTIC SIGNALS

FIELD OF THE INVENTION

The present invention relates to a device and method for extracting information from remotely detected characteristic signals, wherein the characteristic signals are embedded in a data stream derivable from electromagnetic radiation, in particular wherein the data stream comprises a continuous or discrete characteristic signal including physiological information indicative of at least one at least partially periodic vital signal.

BACKGROUND OF THE INVENTION

WO 2011/021128 A2 discloses a method and a system for image analysis, including:
  obtaining a sequence of images;
  performing a vision based analysis on at least one of the sequence of images to obtain data for classifying a state of a subject represented in the images;
  determining at least one value of a physiological parameter of a living being represented in at least one of the sequence of images, wherein the at least one value of the physiological parameter is determined through analysis of image data from the same sequence of images from which the at least one image on which the vision based analysis is performed is taken; and
  classifying a state of the subject using the data obtained with the vision based analysis and the at least one value of the physiological parameter.

The document further discloses several refinements of the method and system. For instance, the use of remote photoplethysmographic (PPG) analysis is envisaged.

WO 2011/042858 A1 discloses a further method and system addressing processing a signal including at least a component representative of a periodic phenomenon in a living being. Additional basic approaches to remote photoplethysmography are described in Verkruysse, W. et al. (2008), "Remote plethysmographic imaging using ambient light" in Optics Express, Optical Society of America, Washington, D.C., USA, Volume 16, No. 26, pages 21434-21445.

Still, the recorded data such as captured reflected or emitted electromagnetic radiation (e.g., recorded image frames) always comprises, beside of the desired signal to be extracted therefrom, further signal components deriving from overall disturbances, by way of example, such as noise due to changing luminance conditions or movement of observed objects. Hence, a detailed precise extraction of the desired signals still poses major challenges for the processing of such data.

Although considerable progress in the field of computing performance has been made, it is still a challenge to provide for instant image recognition and image processing enabling immediate, or, so-to-say, online detection of desired vital signals. This applies in particular to mobile device applications still lacking of sufficient computing power. Furthermore, data transmission capacity can be restricted in several environments. For instance, a lot of mobile users still rely on so-called "pay as you go" mobile contracts. Given the above, there is still a need to keep data volume and computing costs small.

A possible approach to this challenge may be directed to providing well-prepared and steady ambient conditions when capturing a signal of interest in which the desired signal component is embedded so as to minimize disturbing signal components overlaying the signal. However, such laboratory conditions cannot be transferred to everyday field applications as high efforts and preparation work would be required therefore.

After all, vital signal detection is made even more difficult when amplitudes and/or nominal values of disturbing signal components are much larger than amplitudes and/or nominal values of desired signal components to be extracted. In the field of remote PPG, the magnitude of difference between the respective components can be expected to even comprise several orders.

SUMMARY OF THE INVENTION

It is therefore an object of the present invention to provide a system and a method for extracting information from remotely detected characteristic signals providing further refinements facilitating obtaining these desired signals with higher accuracy and preferably with reduced computing efforts.

Furthermore, it would be advantageous to provide a device and method even further adapted for enabling a robust extracting of the desired signals under considerably poor ambient conditions, e.g. a small signal to noise ratio at least partially arising from steady or even unsteady motion of the object to be observed, or from motion of the measurement device itself. It would be further advantageous to provide a device adapted for being less susceptible to disturbances influencing the captured signals to be processed and analyzed.

In a first aspect of the present invention a device for extracting information from remotely detected characteristic signals is presented, the device comprising:
  an interface for receiving a data stream derivable from electromagnetic radiation emitted or reflected by an object, data stream comprising a sequence of frames, at least some of the frames comprising a frame section representative of a region of interest attributable to the object, the region of interest exhibiting a continuous or discrete characteristic signal including physiological information, the physiological information being representative of at least one at least partially periodic vital signal, the sequence of frames further comprising a disturbing signal portion at least partially indicative of undesired object motion, the disturbing signal portion adversely affecting the characteristic signal,
  a stabilizing processing means comprising:
    a converter for deriving a derivative signal form from at least some frames of said sequence of frames through a dimensional reduction, the derivative signal form comprising at least a first signal component and a second signal component indicative of positional information,
    a comparator for estimating a positional shift of a present derivative signal form relative to a previous derivative signal form, the positional shift being representative of undesired object motion,
    a compensator for determining a present frame section under consideration of the estimated positional shift, the present frame section at least partially representing the region of interest, such that the region of interest can be tracked for at least partially compensating undesired object motion,
  an extractor for extracting the characteristic signal from the sequence of frames under consideration of a sequence of determined frame sections, wherein the characteristic signal is associated with a signal space representative of characteristics of the electromagnetic radiation.

Object motion poses major challenges for signal detection, in particular when instant signal detection is demanded and/or when computing capacity is restricted. Still, computing capacity can be considered a bottleneck for vital signal detection, especially when mobile devices are utilized. Furthermore, objection motion may cause illumination changes and related disturbances even further adversely affecting the characteristic signal. Hence, it is beneficial to address motion compensation.

The device presented above is configured for executing an advantageous motion compensation algorithm. Usually, motion compensation requires huge computing capacity and costs. Therefore, instant motion compensation is hard to achieve, especially for mobile devices. For instance, motion compensation could be based on face detection applied to every single frame of a sequence. Consequently, an object to be monitored and observed can be tracked accordingly. However, given the computing performance of common mobile devices, face detection is time consuming and could hardly be implemented for instant detection of vital signals. It should be understood that instant detection as used herein also comprises nearly instant detection. In other words signal detection can be considered instant when a user does not notice a considerable time delay.

It is understood that high priced state of the art mobile devices actually implement face detection approaches. However, these conventional approaches are directed to unique (or: singular) detection runs rather than permanent face detection and tracking. For instance, face detection can be utilized for selectively "unlocking" a locked device. Still, these approaches are prone to errors. By way of example, detection of frontal faces or close to frontal faces under considerably good illumination conditions can be achieved. Apart from that, face detection often fails due to adverse orientation of the object and/or poor illumination conditions.

Therefore, the approach presented above is beneficial in that motion compensation does not require face detection and the like at every frame (or: at a large number of frames). This is achieved by transferring the underlying problem to a fairly simplified "substitute" problem.

For instance, computing time consuming image processing can be transferred into processing of simplified derivative elements. To put it in another way, according to a preferred embodiment, a two-dimensional image processing task can be transferred into two one-dimensional computing tasks.

This approach is based on the insight that at least two characteristic one dimensional patterns derived from a given two-dimensional (image) pattern may comprise sufficient positional information enabling to estimate a positional shift of the object to be observed. Furthermore, the device does not have to be "aware" of the nature of the object to be tracked. Still, positional shift can be estimated through an observation (comparison) of the characteristic one-dimensional patterns over time. For instance, the frame section representing the region of interest can be selected at the beginning of an observation of the object of interest. This selection can be carried out manually or by use of pattern detection algorithms. However, an initial frame section selection can be considered a substantially unique procedure so as to determine a reference section to be tracked. Subsequent motion compensation is based on substitutes of the frames comprising substitutes of the frame section to be tracked. The substitutes, namely the derivative signal forms, are easy to be computed and processed. In particular, it is not necessary to explicitly model the region of interest (which is behind the selected frame section) for every single frame.

It should be noted that commonly known pattern detection approaches basically require that certain distinct regions of an object have to be observed. For instance, a human face can be considered such a distinct region, since eyes, nose and mouth can be detected through conventional algorithms already implemented in several image processing devices, e.g., face detection and/or smile detection functionality of digital cameras. However, the vital signal of interest is also exhibited by different regions of the object which do not necessarily have to contain the object's face. For instance, remote PPG can be applied to skin portions of the face (not the whole face), the neck, arms, or even hands of the object of interest. Consequently, the approach presented above is far more flexible than approaches relying on image per image face detection and the like.

It should be further noted that according to the approach presented above tracking of more than one region of interest can be enabled. The plurality of regions of interest may belong to the same or even to different objects to be observed. Basically, the substitute derivative signal forms still comprise positional information of the whole frame. Therefore, given the comparator and the compensator are adapted accordingly, more than one region of interest can be tracked. To this end, the comparator can be configured for estimating more than one characteristic shift of a present derivative signal form relative to a previous derivative signal form. Accordingly, the compensator can be configured for determining more than one present frame section under consideration of the estimated positional shift(s) of the regions of interest to be tracked.

It should be understood that object motion can comprise motion of the object to be observed with respect to the device and, vice versa, motion of the device with respect to the object of interest. Hence, the term object motion comprises relative motion between the object of interest and the device which can be compensated accordingly.

The sequence of frames can be embodied by a series of image frames comprising color information, such as RGB-images. The image frames can represent the object of interest and further elements. Basically, at least some of the further elements are not indicative of the desired signals to be extracted from the characteristic signals.

There exist several embodiments of the extractor and the stabilizing processing means comprising the converter, the comparator and the compensator. In a first, fairly simple embodiment both, the stabilizing processing means and the extractor are embodied by a processing unit, in particular a processing unit of a mobile device, which is driven (or: controlled) by respective logic commands. Such a processing unit may also comprise suitable input and output interfaces.

However, in the alternative, each of the stabilizing processing means including the converter, the comparator and the compensator, and the extractor can be embodied by separate processing units (or: controlled) or controllable by respective commands. Hence, each respective processing unit can be adapted to its special purpose. Consequently, a distribution of tasks can be applied, wherein distinct tasks are processed (or: executed) on a signal processor of a multi-processor processing unit or wherein image processing related tasks are executed on an image processor while other operational tasks are executed on a central processing unit.

According to an advantageous embodiment, the device further comprises an analyzer for determining temporal variations of the characteristic signal, and for detecting the at least one at least partially periodic vital signal represented by the physiological information embedded in the characteristic signal.

It is reasonable that also the analyzer is embodied by a central processing unit or at least by a part of a multiprocessor processing unit respectively controlled by logical commands. It goes without saying that further signal optimization measures can be applied to the characteristic signal prior to the detection of the at least one at least partially periodic vital signal. In this way, even further disturbing signal components substantially non-indicative of the desired vital signal can be attenuated or even removed from the data stream.

According to a further aspect of the device a converter is configured for agglomerating frame entities along a first direction and along a second direction of the at least some frames of said sequence of frames so as to derive the derivative signal form, wherein the first signal component preferably comprises a dimensional reduced mapping of frame lines, and wherein the second signal component preferably comprises a dimensional reduced mapping of frame columns.

In other words, frame entities can be projected along lines in the first direction and the second direction which comprise different orientations. Preferably, the first direction and the second direction are rectangular to each other (e.g., horizontal and vertical). The projections may comprise integrating or adding up frame entities (e.g. respective RGB values) along lines and columns of the frames.

As used herein, an entity may comprise a single pixel or a sub-agglomeration of pixels. Given the lines and columns of the entities (pixels), the frame can comprise a pixel pattern. In other words, each of the frames can comprise a matrix structure. In the alternative, the frames can also comprise a honeycomb structure. Needless to say, further shapes can be envisaged. The lines and columns of the frames can be arranged in accordance with a coordinate system, preferably a Cartesian coordinate system. Alternatively, also a polar coordinate system, further suitable coordinate systems and their derivates can be utilized.

Needless to say, also a coordinate transformation can be applied to an original frame coordinate system prior to the dimensional reduction. Hence, a frame section to be processed can be transferred into a suitable orientation such that the lines and columns to be processed exhibit plain positional information. For instance, edges attributable to the object (or: to object-background transition) that are present in the frames can be at least substantially orthogonally aligned with the lines or the columns to be processed for the derivation. In general, basically orthogonal (e.g., horizontal or vertical) edges can cause strong positional information signals which can be easily detected and processed. Also high contrast areas attributable to the object cause strong positional information signals.

According to yet another aspect of the device the at least one at least partially periodic vital signal is selected from the group consisting of heart rate, heartbeat, respiration rate, heart rate variability, Traube-Hering-Mayer waves, and oxygen saturation.

Advantageously, at least some of these vital signals can be converted into one another. For instance, the characteristic signal may comprise RGB-values of single pixels or a pixel pattern exhibiting skin color of the object of interest. Slight fluctuations of these values over time can be referred to as the physiological information. Processing and analyzing of the characteristic signal enables the detection of the vital signal(s) of interest. For instance, slight oscillations of the characteristic signals can be analyzed and interpreted so as to arrive at the detection of heart beat or heart rate signals. Furthermore, it should be understood that, in general, the desired vital signal(s) can be derived directly or indirectly from at least one at least partially periodic signal the object of interest exhibits. Needless to say, the device (and method) of the invention can be combined with further detecting and analyzing measures so as to further enhance the extracted signals.

Remote photoplethysmography can make use of several approaches so as to detect the vital signals of interest. For instance, in particular when the frames comprise RGB-values or similar color information, a ratio between red (R) and green (G) signals can be determined. This ratio can be considered highly indicative of the desired signals to be extracted. Furthermore, a normalization can be applied wherein the red and green signals are divided by their respective (temporal) mean values. Normalization can render signal components at least partially independent from overall disturbances. According to an alternative approach, a ratio between red (R) and infrared (IR) signal can be considered attentively for extracting the vital signals of interest.

The vital signal of interest may comprise discrete values, for instance heart rate values (beats per minute). In the alternative, also the signal wave form over time can be of interest so as to allow even further conclusions.

According to another aspect of the device the signal space is a color signal space comprising at least two complementary channels, the at least two complementary channels being related to define spectral positions, wherein the characteristic signal comprises at least two main components, each of which being related to a respective complementary channel.

In an exemplary embodiment, the signal space can be an RGB signal space or a respective derivate. Hence, the signal space can comprise three components representing values of three main components of the characteristic signal. Alternative signal spaces may comprise or be derived from CIE XYZ, HSV, HSL, sRGB and xvYCC signals. Also derivates thereof can be utilized. It should be noted that basically linear RGB signals can be utilized for the desired signal detection. Therefore, non-linear signal spaces (e.g. gamma corrected signals) can be transformed accordingly. It can be further envisaged to combine several distinct signal spaces, at least partially, so as to provide broader spectral basis for the required analyzing processes. For instance, so-called RGBY signals can be applied as well. In an RGBY signal space in addition to red, green and blue, also yellow signals can carry color information. In case the input data stream is related to a subjective color model, e.g., CMYK, the data can be transferred accordingly so as to arrive at an additive signal space. Further spectral components can be utilized for extracting the desired vital signal(s) from the data stream. In this connection, also infrared or near-infrared radiation components can be applied. For instance, a ratio between red and infrared signals can be highly indicative of the desired signals.

It is further preferred that the signal space is configured such that the at least partially periodic vital signal is embedded in slight temporal fluctuations of at least one of the at least two main components of the characteristic signal.

According to yet another embodiment of the device for extracting information, the converter is further configured for deriving a reference derivative signal form from a frame of said sequence of frames during an initial stage, the reference derivative signal form comprising at least a first reference component and a second reference component indicative of reference positional information, and wherein the comparator is further configured for estimating the positional shift of each of plurality of subsequent derivate signal forms during a subsequent stage relative to the reference derivative signal form.

In other words, the derivative signal form of each of a plurality of subsequent frames can be traced back (or: linked) to a single (or: static) reference frame processed at the beginning of the signal processing procedure. For instance, the first frame of the sequence can be processed so as to derive the (static) reference derivative signal form. Hence, the reference derivative signal form (or: the first reference component and the second reference component) can be buffered so as to provide a steady basis for the stabilizing processing. In this way, a "rolling" processing procedure utilizing requiring a permanent calculation of varying derivative signal forms as references can be avoided.

This is beneficial in that corrupted frames cannot serve as a basis for deriving the reference derivative signal form which can impede determining succeeding frame sections for succeeding frames. As used herein, corrupted frames can be considered to comprise an erroneous representation of the region of interest. For instance, corrupted frames can comprise occlusions, e.g., further objects hiding the object of interest. Corrupted frames can be adversely affected by (image) interferences, for instance noise and such like. Furthermore, in a corrupted frame the object of interest could be positioned out of the captured area of the frame. Moreover, the object of interest could be orientated in an adverse way in a corrupted frame, for instance, bent, twisted or turned.

In this connection, it is preferred that the device further comprises a buffer means adapted for buffering the reference derivative signal form throughout the whole processing procedure. In this way, a steady basis for shift estimation and motion compensation can be provided. It is not necessary to derive the reference derivative signal form from a frame having a set interval (or: sequence spacing) to each present frame of the sequence to be processed.

This embodiment can be further developed in that the stabilizing processing means is further configured for triggering the converter means such that at least a further reference derivative signal form can be derived from a frame during a subsequent stage.

By way of example, trigger events can be selected from the group comprising past time periods, a number of processed frames and further process parameters. Therefore, trigger events can be basically periodic. On the other hand, non-periodic triggering can be applied. For instance, the converter means can be triggered to derive a new reference derivative signal in the event that a certain number of corrupted frames has been processed. Further quality-related trigger events can be envisaged. In this way, the processing procedure can be split into several sub-terms each of which having a reference frame comprising a reference derivative signal serving as a basis for positional shift estimation during that particular term. Preferably, also manual triggering can be allowed. In this way, a user can re-initiate (or: refresh) the signal processing procedure.

According to another embodiment of the device the stabilizing processing means further comprises a pattern detector for determining a frame section at least partially representing the region of interest in at least one frame of said sequence of frames during an initial stage such that an initial frame section can be determined as a reference frame section.

It should be understood that also in this embodiment pattern detection is merely required for a single frame or a small number of frames (e.g. the reference frames) in relation to the absolute number of processed frames.

Preferably, the pattern detector can be coupled to the stabilizing processing means such that triggering the converter also triggers an (automatic) pattern detection. For instance, this can be initiated when displacement estimation fails due to corrupted frames. The pattern detector can be configured for face detection, skin detection, etc.

According to yet another embodiment the stabilizing processing means further comprises a biasing means for correcting estimated positional shift values under consideration of present absolute shift estimates and/or temporal consistency of present shift estimates.

The correction of estimated positional shift values can comprise a reduction of impacts on shift values deriving from considerably large offsets and/or temporal inconsistent displacement estimates. Several assumptions can be considered for applying a bias function some of which will be presented below.

According to a further preferred aspect the device comprises an integrated sensor means capable of capturing the data stream comprising the sequence of frames.

Preferably, the device is a mobile device, such as a mobile phone, a personal digital assistant (PDA), a mobile computer, a mobile tablet, and/or a mobile single-purpose or multi-purpose medical scanning or monitoring device. Furthermore, the device can be positioned in a vehicle, either as an integral part or as a detachable vehicle installation.

According to another embodiment the device for extracting information further comprises a filter for selectively attenuating or enhancing components of the characteristic signal.

For instance, a frequency filter can be utilized for enhancing a signal component at a bandwidth between 0.05 Hz and 10 Hz, preferably between 0.5 Hz and 3.5 Hz. This can be considered a particularly appropriate range for heart beat measurement. For respiration rate measurement, for instance, the range can comprise frequency values between about 0.1 Hz and about 2 Hz. For the detection of Traube-Hering-Mayer waves, the range can comprise frequency values between about 0.05 Hz and about 0.2 Hz. Post-filtering of the processed signal can further improve the signal-to-noise ratio. In this way, even further disturbing signal components non-indicative of the desired vital signals can be removed from the data stream.

In the alternative, or in addition, a recursive temporal filter can be applied. For instance, the device can further comprise a weighting means for selectively influencing components of the characteristic signal. In this connection, it is recalled that the vital signal of interest is considered to be embedded in slight fluctuations of physiological information represented by the characteristic signals. Overall disturbances can be expected to be much larger in magnitude than the desired signals of interest.

In a further aspect of the present invention a method for extracting information from remotely detected characteristic signals is presented, comprising the steps of:

receiving a data stream derivable from electromagnetic radiation emitted or reflected by an object, the data stream comprising a sequence of frames, at least some of the frames comprising a frame section representative of a region of interest attributable to the object, the region of interest exhibiting a continuous or discrete characteristic signal including physiological information, the physiological information being representative of at least one at least partially periodic vital signal, the sequence of frames further comprising a disturbing signal portion at least partially indicative of undesired object motion, the disturbing signal portion adversely affecting the characteristic signal, stabilizing the characteristic signal, comprising:

deriving a derivative signal formed from at least some frames of said sequence of frames through a dimensional reduction, that the derivative signal form comprising at least a first signal component and a second signal component indicative of positional information, estimating a positional shift of a present derivative signal form relative to a previous derivative signal form, the positional shift being representative of undesired objection motion, determining a present frame section under consideration of the estimated positional shift, the present frame section at least partially representing the region of interest, such that the region of interest can be tracked for at least partially compensating undesired object motion, and extracting that characteristic signal from the sequence of frames under consideration of a sequence of determined frame sections, wherein the characteristic signal is associated with a signal space representative of characteristics of the electromagnetic radiation.

Advantageously, the method can be carried out utilizing the device for extracting information of the invention.

According to an embodiment the method further comprises the steps of:

deriving a reference derivative signal formed from a frame of said sequence of frames during an initial stage, wherein the reference derivative signal form comprises at least a first reference component and a second reference component indicative of reference positional information, and estimating the positional shift of each of a plurality of subsequent derivative signal forms during a subsequent stage relative to the reference derivative signal form.

In this way, a loop function having a set (or: static) reference basis segment can be established. No "rolling wave" control loop is required. Since the loop function basically relies on available reference values, reduced computation resources are required.

In yet another aspect of the present invention, there is provided a computer program which comprises program code means for causing a computer to perform the steps of the processing method when said computer program is carried out on a computer.

As used herein, the term computer stands for a large variety of processing devices. In other words also mobile devices having a considerable computing capacity can be referred to as computing device though they provide less processing power resources than standard desktop computers.

Preferred embodiments of the invention are defined in the dependent claims. It should be understood that the claimed methods and the claimed computer program have similar preferred embodiments as the claimed device and as defined in the dependent device claims.

BRIEF DESCRIPTION OF THE DRAWINGS

These and other aspects of the invention will be apparent from and elucidated with reference to the embodiment(s) described hereinafter. In the following drawings

FIG. 5a shows a frame to which a derivative signal form derivation is applied;

FIG. 5b shows a further frame having a frame section representing a region of interest of an object which is shifted with respect to a respective position shown in FIG. 5a;

DETAILED DESCRIPTION OF THE INVENTION

The following section describes exemplary approaches to remote photoplethysmography utilizing several aspects of the device and method of the invention. It should be understood that single steps and features of the shown approaches can be extracted from the context of the respective overall approach. These steps and features can be therefore part of separate embodiments still covered by the scope of the invention.

Figure 1:
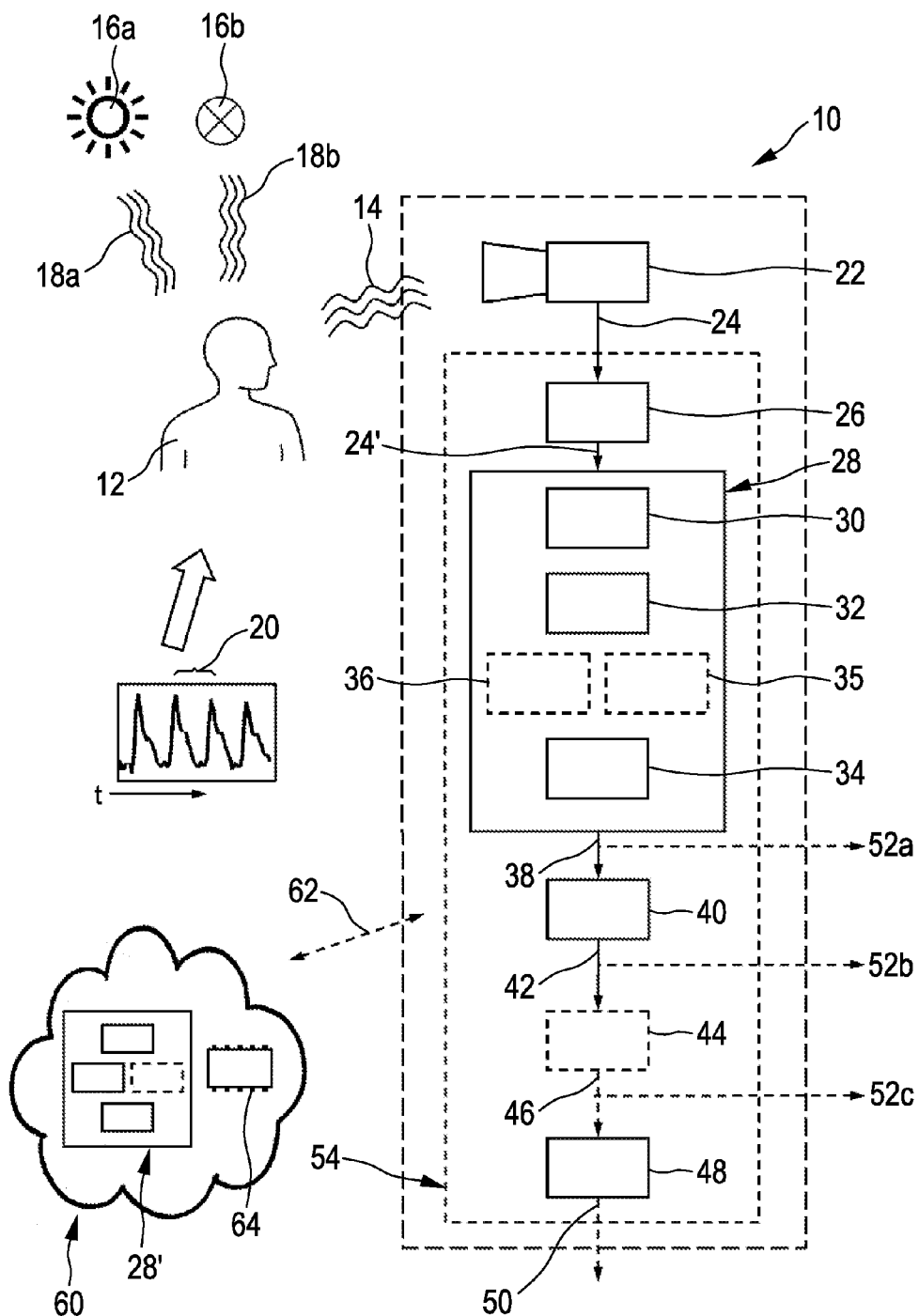
FIG. 1 shows a schematic illustration of a general layout of a device in which the present invention can be used.

FIG. 1 shows a schematic illustration of a device for extracting information which is denoted by a reference numeral 10. For instance, the device 10 can be utilized for recording image frames representing a remote object 12 for remote PPG monitoring. The image frames can be derived from electromagnetic radiation 14 emitted or reflected by the object 12. The object 12 can be a human being or animal, or, in general, a living being. Furthermore, the object 12 can be part of a human being highly indicative of a desired signal, e.g. a face portion or, in general, a skin portion.

A source of radiation, such as sunlight 16a or an artificial radiation source 16b, also a combination of several radiation sources can affect the object 12. The radiation source 16a, 16b basically emits incident radiation 18a, 18b striking the object. For extracting information from the recorded data, e.g., a sequence of image frames, a defined part or portion of the object 12 can be detected by a sensor means 22. The sensor means 22 can be embodied, by way of example, by a camera adapted for capturing information belonging to at least a spectral component of the electromagnetic radiation 14. Needless to say, the device 10 also can be adapted to process input signals, namely an input data stream, ready recorded in advance and, in the meantime, stored or buffered. As indicated above, the electromagnetic radiation 14 can contain a continuous or discrete characteristic signal which can be highly indicative of at least one at least partially periodic vital signal 20. The characteristic signal can be embedded in an (input) data stream 24. According to one embodiment, for data capturing, a potentially highly indicative portion of the object 12 can be selected (or: masked with a pixel pattern). When agglomerating respective signal pixel values of the pixel pattern at an instant, a mean pixel value can be derived from the pixel pattern. In this way, the detected signals can be normalized and compensated for overall disturbances to some extent. The mean pixel value can be represented by a characteristic signal. The vital signal of interest 20 can be embedded in slight fluctuations (slight periodic property changes) of the characteristic signal. In the following, the captured data stream 24 can be considered a representation of a certain area of interest of the object 12 which may cover an agglomerated pixel area covering a plurality of pixels. In FIG. 1 the vital signal 20 may allow several conclusions concerning heart rate, heartbeat, heart rate variability, respiratory rate, or even oxygen saturation.

Known methods for obtaining such vital signals may comprise tactile heart rate monitoring, electrocardiography or pulse oxymetry. To this end, however, obtrusive monitoring was required. As indicated above, an alternate approach is directed to unobtrusive remote measuring utilizing image processing methods.

The data stream 24 comprising the continuous or discrete characteristic signal can be delivered from the sensor means 22 to an interface 26. Needless to say, also a buffer means could be interposed between the sensor means 22 and the interface 26. Downstream of the interface 26 a stabilization processing means 28 is provided which is adapted for signal processing of the received data stream 24'. Basically, signal processing can be directed to motion compensation. Undesired object motion or motion of the sensor means 22 with respect to the object 12 can still pose major challenges to vital signal detection approaches. Motion compensation algorithms per se are commonly known but, however, generally require considerable computation efforts. Especially for mobile devices there is a need for improved motion compensation approaches requiring less computing costs.

In accordance with an embodiment of the present invention, the stabilization processing means 28 comprises a converter 30, a comparator 32 and a compensator 34. Each of the converter 30, the comparator 32 and the compensator 34 can be embodied by the same or distinct processing units. In other words, according to an exemplary embodiment, each of the converter 30, the comparator 32 and the compensator 34 can be comprised in a logical portion of the same processing unit.

As indicated by dashed boxes 35, 36, the stabilization processing means 28 can further comprise a pattern detector 35 and/or a biasing means 36. Both the pattern detector 35 and the biasing means 36 can be embodied in a similar way as the converter 30, the comparator 32 and the compensator 34.

Assuming that the input data stream 24, 24' comprises a sequence of frames, the converter 30 can be configured for deriving a derivative signal form from at least some frames of said sequence of frames. The derivative signal form can be dimensionally reduced such that further processing directed to motion compensation can be simplified. The comparator 32 can be configured for estimating a positional shift between a present derivative signal form and a previous derivative signal form. The positional shift can be representative of object motion to be compensated. As mentioned above, the previous derivative signal form can be stored and kept in a buffer for processing more than one subsequent frame of the sequence based on this distinct (static) derivative signal form. Hence, at least part of the comparison algorithm, namely the derivation of a reference derivative signal forms needs to be executed only once during an initial stage.

The compensator 34 can be adapted for determining a present frame section (e.g., a present pixel pattern representative of a region of interest of the object 12) based on an estimated positional shift. The region of interest can be tracked in this way for compensating undesired object motion. It is worth to be mentioned that the compensator 34 does not have to be "aware" of what is behind the present frame section. Comparing a present derivative signal form with a previous derivative signal form basically comprises a comparison of derivates (or: substitutes) which do not clearly exhibit or represent a plane representation (e.g. visible image representation) of the region of interest. In other words, a derivative signal form can be derived from a frame while, in general, a frame cannot be derived from a respective derivative signal form, since the derivative signal form is reduced in dimension. Hence, pattern detection or face detection is not required for every single frame to be compared for motion estimation.

Still, however, the stabilization processing means 28 can comprise a pattern detector 35 which is adapted for pattern detection such as face detection and/or skin detection. According to a preferred embodiment the pattern detector 35 is merely required for an initial stage of a motion compensation procedure so as to detect a certain frame section representative of the region of interest in a frame which serves as a basis for subsequently determining respective frame sections in subsequent frames under consideration of the estimated positional shift.

In an alternative embodiment pattern detection can be performed manually by a user of the device. For instance, the user can mask a face portion or skin portion of the object 12 on a screen representing an initial frame for determining the initial frame section.

The biasing means 36 can be configured for further refining the positional shift estimation. Exemplary biasing functions which can be implemented in the biasing means 36 will be introduced and explained further below.

For instance, the stabilization processing means 28 (more precisely: the comparator 32) can be adapted to apply several matching functions to the obtained derivative signal form components. As indcted above, the derivative signal form can be obtained through integral projections along a first and second direction of the (image) frames. In this regard, reference is also made to FIGS. 5a and 5b. The derivative signal form components derived in this way can be referred to as projection profiles. The comparison of these projection profiles can be performed under different offsets using various match functions. For example, statistical measures such as a correlation function can be applied. In a preferred embodiment a sum or mean of absolute differences can be used. By way of example, displacement along the first and the second direction (e.g., horizontal and vertical direction, or x-direction and y-direction) can be estimated from the integral projections as follows:

$$dx(t) = \arg\min_d \left[ \frac{\sum_{x \in S(d)} |Pref_{hor}(x-d) - Pt_{n,hor}(x)|}{\|S(d)\|} \right], \quad (1)$$

and $$dy(t) = \arg\min_d \left[ \frac{\sum_{X \in S(d)} |Pref_{ver}(x-d) - Pt_{n,ver}(x)|}{\|S(d)\|} \right], \quad (2)$$

wherein the term Pref(x) denotes a reference derivative signal from component (or: reference projection) entity. The term $Pt_n(x)$ denotes a (present) derivative signal from component (or: currently processed projection) entity. The indices ver and hor stand for the first direction and the second direction. The term S(d) denotes support, i.e., an overlap between a derivative signal component (or: projection profile) and a respective reference (signal) component (or: reference projection profile). A support value $\|S(d)\|$ basically depends on an actual offset d which stands for an estimated shift in the respective direction.

This approach can be further developed in that at least one biasing function (or: regularization function) is applied to the estimation algorithm so as to further enhance signal quality. For instance, a term $F_{sup}$ can be added introducing a penalty for considerably large offsets. Such offsets are often of minor value for the estimation since they are less reliable. By way of example, $F_{sup}$ can be computed as follows:

$$F_{sup}(d) = C_{sup} \frac{d}{d_{max}}, \quad (3)$$

wherein $C_{sup}$ is a constant defining a penalty value for the maximum shift detected $d_{max}$.

In the alternative, or in addition, a term $F_{temp}$ can be added introducing a penalty for temporally inconsistent (or: unsteady) shift estimates. For instance, $F_{temp}$ can be calculated as follows:

$$F_{temp}(d(t-1), d) = C_{temp} \exp\left( \frac{-(d(t-1)-d)^2}{\sigma_{temp}^2} \right), \quad (4)$$

wherein $C_{temp}$ is a constant for temporal influences, wherein t denotes time (or: actual frame number) and wherein $\sigma_{temp}$ is the standard deviation of the expected shift estimate.

Equations (1) and (2) can be refined accordingly:

$$dx(t) = \arg\min_d \left[ \frac{\sum_{X \in S(d)} |Pref_{hor}(x-d) - Pt_{n,hor}(x)|}{\|S(d)\|} + F_{sup}(d) + F_{temp}(dx(t-1), d) \right], \quad (5)$$

and $$dy(t) = \arg\min_d \left[ \frac{\sum_{X \in S(d)} |Perf_{ver}(x-d) - Pt_{n,ver}(x)|}{\|S(d)\|} + F_{sup}(d) + F_{temp}(dy(t-1), d) \right]. \quad (6)$$

Consequently, robustness and stability of the displacement estimation can be improved and therefore compensation for undesired object motion can be even further enhanced. It should be understood that the exemplary equations (1) to (6) and the underlying algorithmic approach can be applied mutatis mutandis to the several embodiments described herein.

Downstream of the stabilization processing means 28, an extractor 40 can be comprised in the device 10. A processed compensated data stream 38 can be transferred to the extractor 40. The extractor 40 can be configured for extracting the (processed) characteristic signal from the sequence of frames (or: the sequence of determined frame sections) still comprised in the processed compensated data stream 38. For instance, the characteristic signal to be extracted can be composed of actual RGB values obtained through an agglomeration of skin pixel values contained in the region of interest. Slight fluctuations of the characteristic signal over time can comprise physiological information from which eventually the desired signal 20 can be extracted.

According to another alternative embodiment, the device 10 can further comprise a filter 44 indicated by a dashed box to which an extracted data stream 42 can be transferred. The filter 44 can be configured for enhancing a frequency portion which is expected to contain the desired signal 20.

In the alternative, or in addition, temporal filtering can be applied to the characteristic signals embedded in the processed compensated data stream 38 or the extracted data stream 42. Assuming that in general large changes (or: fluctuations) of the characteristic signals (e.g. color changes) are not attributable to the vital signals of interest, these changes can be considered undesired distortions and therefore suppressed. For instance, recursive temporal filtering can be applied to the signals so as to further enhance signal quality:

$$v'_{x,y}(t) = K(v_{x,y}(t), v'_{x,y}(t-1)) \cdot v_{x,y}(t) + \quad (7)$$
$$(1 - K(v_{x,y}(t), v'_{x,y}(t-1))) \cdot v'_{x,y}(t-1),$$

with $$K(v_a, v_b) = \exp\left( \frac{-(v_a - v_b)^2}{\sigma_v^2} \right), \quad (8)$$

wherein x and y stand for an actual position of a single entity $v_{x,y}$ of the frame section tracked and observed over time t. Again, t can denote time or an actual frame number. The entity may comprise single pixels or subsets of agglomerated pixels. A component K is introduced for applying a weight to each entity $v_{x,y}$, the weight depending on the magnitude of change the entity $v_{x,y}$ undergoes. As an effect entities $v_{x,y}$ subjected to little changes can be processed (e.g. update of actual position) while entities $v_{x,y}$ subjected to large changes can be ignored so that a previous position is kept. Needless to say, the exemplary equations (7) and (8) and the underlying algorithmic approach can be applied mutatis mutandis to the several embodiments described herein.

Downstream of the optional filter 44 a filtered data stream 46 can be transferred to an analyzer 48 which is configured for detecting the at least one at least partially periodic vital signal 20 of interest. For instance, the analyzer 48 can be adapted for detecting dominant signal peaks, such as heart rate indicative frequency peaks. Eventually, an output signal 50 can be obtained.

Dashed arrows 52a, 52b, 52c illustrate that preprocessed data can be output at several stages of the device 10 for further processing outside of the device 10. The data that can be delivered via the arrows 52a, 52b, 52c can be stored or buffered for subsequent processing. Furthermore, output data can be utilized for representing the (image) data stream.

The stabilization processing means 28, the extractor 40, the (optional) filter 44 and the analyzer 48 can be jointly embodied by a common processing unit 54, for instance, a central processing unit having a single processor or multiple processors. Also the interface 26 can be connected thereto in a common processing unit 54 housing the respective subcomponents. By way of example, the processing unit 54 can be implemented in a mobile computing device driven (or: controlled) by respective logic commands and software code. The stabilization processing means 28, the extractor 40, the (optional) filter 44 and the analyzer 48 can be embodied in a "virtual" way by the processing unit 54. In case also the sensor means 22 is jointly connected to the interface 26, a common case may house the respective subcomponents. Such a mobile device 10 can be a mobile phone, a mobile computer in general, a tablet and a mobile remote PPG scanner (refer to FIG. 3).

It should be understood that the device 10 can be further adapted to carry out additional preprocessing or post-processing of the received data such as to even further enhance signal quality.

It is worth noting that at least part of the signal processing can be executed in a remote environment. In FIG. 1 an arrow 60 indicates that at least part of the stabilization processing means 28, the extractor 40, the (optional) filter 44 and the analyzer 48 can be (virtually) embodied by a cloud computing device 60. For instance, the cloud 60 comprises an exemplary alternative stabilization processing means 28' which can take over part of the computing tasks for tracking the desired frame sections. In other words, the cloud 60 can serve as a remote virtual processing unit, as indicated by an exemplary processor 64 in the cloud 60. Data transfer from and to the cloud 60 can comprise wireless data transfer, as indicated by a dashed arrow 62. In the alternative, data transfer can also comprise cable transfer via wire cable networks.

In general, the concepts of "virtual" and "cloud computing" include the utilization of a set of shared computing resources (e.g. servers) which are typically consolidated in one or more data center locations. For example, cloud computing systems may be implemented as web services enabling a user to launch and manage computing resources (e.g. virtual server instances) in third party data centers. In a cloud environment, computer resources may be available in different sizes and configurations so that different resource types can be specified to meet specific needs of several users. Cloud computing may offer flexible resources without having to manage the purchase and operation of additional hardware resources at the (final) user's end. A cloud-based computing resource is considered to exist or execute somewhere in the "cloud", which may be accessed via an internal corporate network or wire public internet. From the perspective of an application developer or information technology administrator, cloud computing enables the development and deployment of applications that exhibit scalability (e.g., increased or decreased resource utilization on demand), performance (e.g., execute efficiently and fast), and reliability (e.g., never, or at least rarely, facing down time), all without any regard for the nature or location of the underlying infrastructure.

As mentioned above, remote PPG measurements relying on a remote detection of blood volume pulsations in an object of interest are very sensitive to object motions. For instance, object motion can be harmful to the desired signal detection in that the object 12 to be observed simply gets out of sight. This applies in particular to hand held devices. However, given that the object 12 remains in sight, object motion can modulate incident radiation reflected from the object's skin. Furthermore, common vital signal detection approaches basically rely on pattern detection or selection of a certain region of interest of the object 12 to be observed. It is therefore desirable to select a frame section representing a region of interest which exclusively or almost exclusively comprises skin pixels. Consequently, often merely small sections of a given frame can be selected for processing. The smaller a given section the greater are (adverse) motion influences.

Figure 2A:
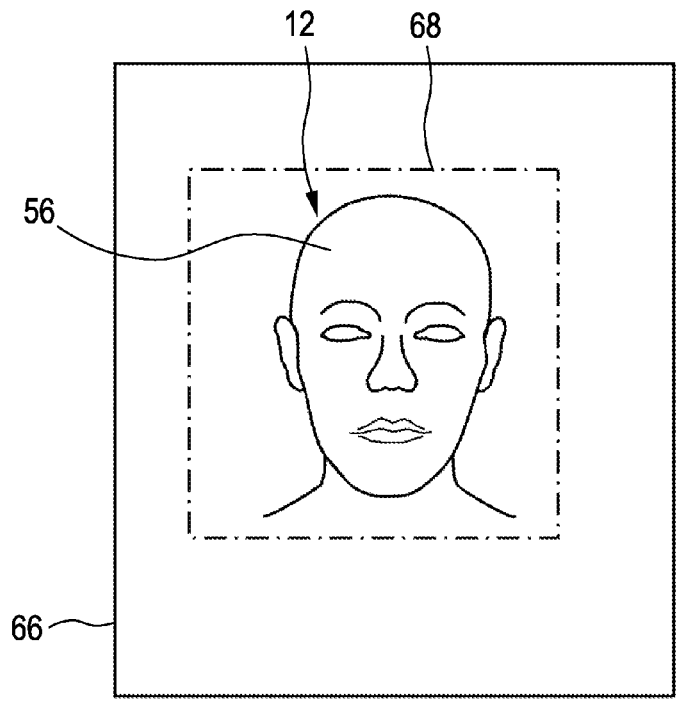
FIGS. 2a, 2b show frames having frame sections representing a region of interest.
Figure 2B:
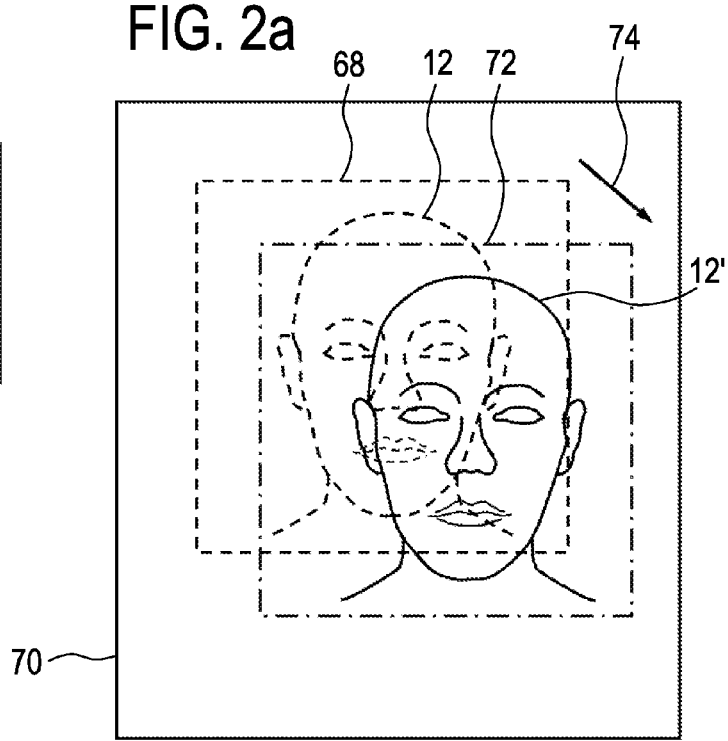

In this connection, FIG. 2a and FIG. 2b exemplarily illustrate single frames 66, 70 taken from a sequence of frames. The frame 66 can be considered a frame captured during an initial stage of a vital signal detection procedure. The frame 66 comprises a frame section 68 representing a region of interest 56 attributable to an object 12 to be observed. For instance, the region of interest 56 can comprise a person's face, or at least a part of the face. In general, the region of interest comprises a skin portion of the object 12. The frame 70 illustrated in FIG. 2b represents a subsequent frame. It should be understood that the subsequent frame 70 is not necessarily a frame immediately succeeding the initial frame 66. The frame 70 comprises a frame section 72 still representing the region of interest 56 of the (meanwhile displaced) object 12'. An initial position of the object 12 is represented by dashed lines. An arrow 74 illustrates a shift or displacement of the object 12 or the respective frame sections 68, 72.

As used herein, a frame may cover the whole field of view that can be captured by a sensor means (e.g. a camera). However, according to some embodiments the frame may comprise merely a subset of an overall frame the sensor means can capture.

Conventional motion compensation algorithms basically require to detect the region of interest 56 in every single frame 66, 70 so as to determine the shift 74. Based on this costly computation the frame sections 68, 72 can be selected for further processing so as to extract the vital signal 20 of interest. In the following, an alternative approach for object motion compensation in remote PPG devices will be illustrated and explained.

Figure 3:
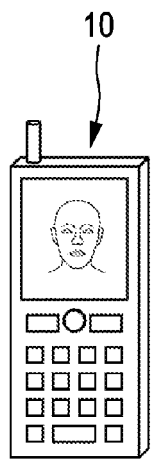
FIG. 3 shows an exemplary mobile device in which the present invention can be used, FIG. 4 schematically illustrates a frame having a certain frame section to which a coordinate transformation can be applied.

An exemplary remote PPG device 10 is illustrated in FIG. 3. For instance, the device 10 can be implemented by a mobile phone, a mobile tablet device, or a mobile medical monitoring device. The device 10 can be considered a hand-held device. Preferably, the device is configured for showing a representation of the object to be observed to a user. It is further preferred that the device 10 is configured for manually and/or automatically selecting the initial frame section 68 in an initial frame 66 during an initial stage of the signal processing procedure.

Figure 4:
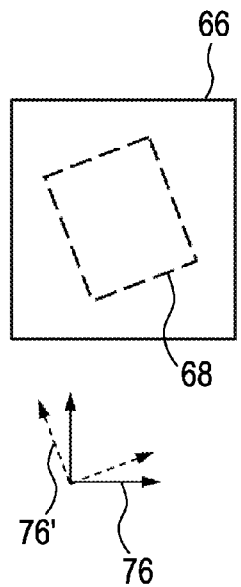

FIG. 4 shows a schematic alternative representation of an exemplary frame 66 in which a frame section 68 has been selected. For instance, the frame 66 is aligned with a reference coordinate system 76. By contrast, the selected frame section 68 can be aligned with a tilted coordinate system 76'. Needless to say, the coordinate systems 76, 76' can be converted into each other through suitable transforming processes. It is worth mentioning that neither the frame 66 nor the selected frame section 68 necessarily have to be shaped as rectangular boxes. In particular, the selected frame section 68 can exhibit a different shape which is suitably adapted to a given region of interest.

Conventional motion compensation approaches including pattern detection (face detection) applied to each and every single frame often fail when determining relative shifts between two consecutive frames. This could happen in case the region of interest is occluded or even out of sight in at least one of the processed frames. Since conventional motion compensation approaches utilize rolling shift estimation stepwise applied to consecutive frames (with reference to respective frames having a set, i.e. constant, relative gap to the respective frames), both the respective reference frames and the respective "present" frames to be processed are rolling. In other words the reference frame can be a direct or indirect predecessor of a current frame to be processed. The conventional approaches show poor performance when regions of interest are at least partially and temporarily occluded. Basically, the rolling motion compensation algorithm can collapse when a single frame comprises a somehow corrupted region of interest while all further frames exhibit proper shaped regions of interest. Recovering of conventional motion compensation algorithms after such failures is hard to achieve and requires substantial computing efforts.

Given the drawback inherent to conventional motion compensation approaches, it would be desirable to provide a robust motion compensation approach for remote photoplethysmography being less sensitive to frames comprising corrupted frame sections and requiring less computational costs.

Such an approach can be outlined below. Reference is made to FIGS. 5a and 5b illustrating frames 66, 70 similar to the frames 66, 70 shown in FIGS. 2a and 2b. FIG. 5a shows the initial frame 66 and FIG. 5b shows a subsequent frame 70. Again, the object 12 to be observed has moved in FIG. 5b (refer to reference numeral 12') with respect to its initial position. Accordingly, a frame section 68 of FIG. 5a representing an area which is to be chosen for vital signal extraction should be moved as well so as to track the region of interest (e.g. the face) of the object 12, refer to the (shifted) frame section 72 in FIG. 5b. The shift or displacement is represented by an arrow 74. The arrow 74 can be considered a displacement vector. It would be advantageous to determine or, at least, estimate the shift vector 74 without applying pattern detection to the object 12 for each subsequent frame 70.

To this end, a dimensionally reduced representation of the initial frame 66 is created. Referring again to FIG. 5a, a first frame direction 80 (e.g. lines or horizontal lines) and a second frame direction 82 (e.g. columns or vertical lines) are indicated by respective arrows. For instance, the first direction 80 and the second direction 82 may coincide with the respective axis of the coordinate system 76 (refer to FIG. 4). Image entities can be agglomerated (e.g. integrated) along lines in the first direction 80 and along columns in the second direction 82. Consequently, an agglomeration along the first direction 80 can lead to a first component 78a of a derivative signal form 78. The agglomeration along the second direction 82 can generate a second derivative signal form component 78b. For instance, the first derivative signal form component 78a can be embodied by a first one-dimensional index element 84 having a certain density or weight distribution. Accordingly, the second derivative signal form component 78b can be embodied by a second one-dimensional index element 86 having a certain density or weight distribution. As mentioned above, agglomerating pixel entities either in the first direction 80 or in the second direction 82 may comprise adding up respective RGB (channel) values or similar color property values along each line or column. In a preferred embodiment, only values of a single channel need to be agglomerated for detecting the desired signals. For instance, in an RGB environment, the G channel can be considered highly indicative. In an YUV environment, the Y channel can be considered highly indicative.

In this way a density or weight of each entity on the first one-dimensional index element 84 and the second one-dimensional index element 86 can be determined. The number of entities at the first index element 84 can correspond to the number of lines 80 of the frame 66. The number of entities at the second index element 86 can correspond to the number of columns 82 of the frame 66.

Assuming that the object of interest 12 exhibits considerably plain edges and/or high contrast areas in comparison with the background and surrounding objects, the derivative signal form 78 comprising of the first derivative signal form component 78a and the second derivative signal form component 78b can comprise clear positional information. By way of example, the first derivative signal form component 78a can exhibit a substitute vertical position information. Hence, the second derivative signal form component 78b can comprise substitute horizontal positional information. The derivative signal form 78 of the initially processed frame 66 can be used as a reference derivative signal form 78 comprising a first reference derivative signal form component 78a and a second reference derivative signal form component 78b.

In each of a sequence of succeeding frames 70, the reference derivative signal form 78 can be used as a reference for positional shift estimation. To this end, also in FIG. 5b the frame 70 is processed such that a present derivative signal form 88 comprising a first derivative signal form component 88a and a second derivative signal form component 88b can be obtained. Since the object 12' is displaced in frame 70, also the derivative signal form components 88 a, 88b are shifted accordingly.

FIG. 5b further comprises schematic representations of the first and second reference derivative signal form components 78a, 78b indicated by dashed lines. The derivative signal form components 78a, 78b remain in position (refer to the dashed line representation of the object 12 in FIG. 5b) such that a clear shift of the first and second present derivative signal form components 88a, 88b with respect to the first and second reference derivative signal form components 78a, 78b can be estimated. An exemplary approach is shown above in connection with equations (1) and (2).

The estimated shift or displacement is represented by a shift vector 74. The shift 74 can be composed of a first shift component 74a (e.g., vertical shift) and a second shift component 74b (e.g., horizontal shift). The first shift component 74a describes the relative shift between the first reference derivative signal form component 78a and the first present derivative signal form component 88a. The second shift component 74b describes the shift between the second reference derivative signal form component 78b and the second present derivative signal form component 88b.

Having estimated the shift vector 74, the present frame section 72 assumingly comprising the desired region of interest of the object 12' can be determined. Again, it is worth mentioning that the present frame section 72 can be determined without facing the need to actually detect or rebuild the representation of the moved object 12' in the frame 70. Consequently, motion compensation can be performed irrespective of an actual frame content. The proposed algorithm is robust and can provide an anti-shake functionality. Therefore, also hand-held devices 10 (refer to FIG. 3) can be utilized for detecting and extracting the desired signals.

Figure 6:
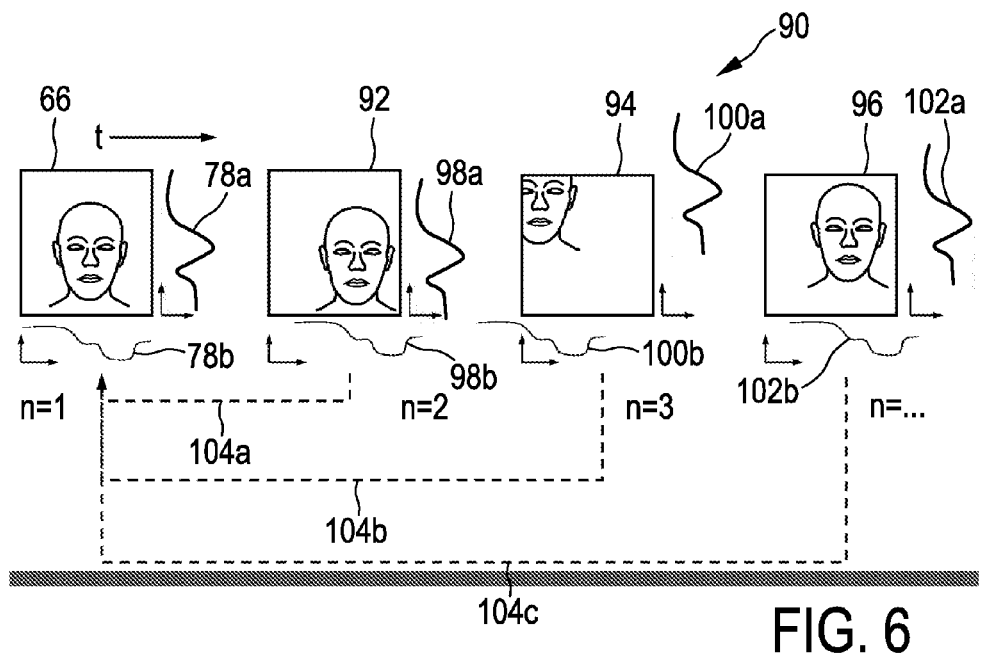
FIG. 6 shows a sequence of frames representing a moving object.

FIG. 6 shows an exemplary sequence 90 of image frames 66, 92, 94, 96. For instance, a remote PPG measurement may comprise a duration of about 10 to 40 seconds, preferably of about 30 seconds. The sequence of frames to be processed can be captured at a refresh rate (or: frequency) of about 20 to 40 frames per second, preferably of about 30 frames per second.

As discussed earlier in connection with FIGS. 5a and 5b, each of the subsequent frames 92, 94, 96 can be traced back to the reference frame 66 for motion compensation measures. For instance, initial frame 66 (n=1) can be considered the reference frame from which the reference derivative signal form 78a, 78b can be derived, refer to FIG. 5a. Each of the subsequent frames 92, 94, 96 (n=2, 3, . . . ) can be processed so as to derive respective derivative signal forms 98, 100, 102 each of which may comprise a first component 98a, 100a, 102a and a second component 98b, 100b, 102b. Dashed lines 104a, 104b, 104c indicate that each of the derivative signal forms 98, 100, 102 can be traced back to the reference derivative signal form 78 for estimating each respective shift with respect to the reference frame 66. In this way, each of the (substitutes of the) subsequent frames 92, 94, 96 can be compared to a proper reference. There is no risk of basing a shift estimation on a corrupted reference. Furthermore, given that some of the subsequent frames 92, 94, 96 could be corrupted, still each following "working" frame which is not corrupted can be processed. Consequently, the motion compensation algorithm can easily recover after failures.

Figure 7:
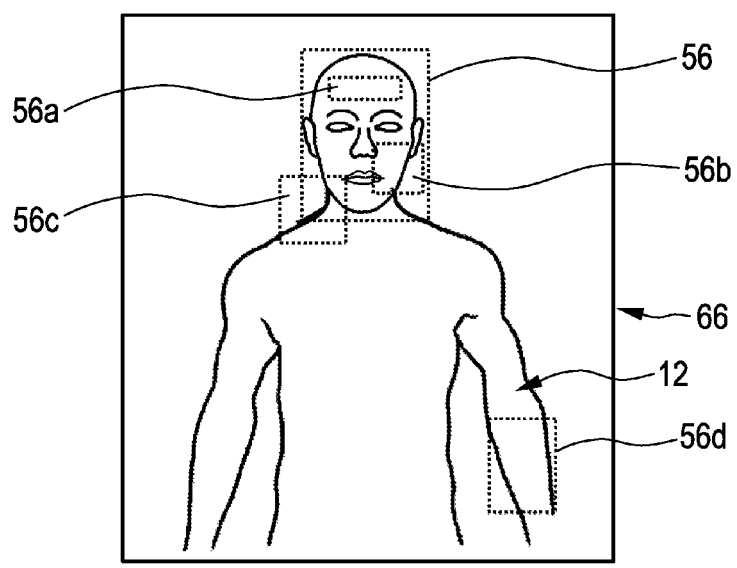
FIG. 7 shows a further frame representing an object in which exemplary regions of interest are illustrated

FIG. 7 shows an (image) frame 66 exhibiting a representation of the object 12. As mentioned above, several portions of the object 12 to be observed may serve as a region of interest 56 highly indicative of the desired vital signals. For instance, a face portion as a whole can be represented in a region of interest 56. However, remote photoplethysmographic vital signal detection can also be applied to smaller regions of interest. For instance, a region of interest 56a can comprise a forehead portion of a face. An alternative region of interest 56b can comprise a cheek portion of a face. Furthermore, a region of interest 56c can comprise a neck portion. A further alternative region of interest 56d basically comprises a forearm portion of the object 12 to be observed. Also a hand portion of the object 12 can be observed as a region of interest. The presented approach does not necessarily require to be applied to a face portion of the object 12. Since motion compensation is basically performed despite of what actually is the region of interest 56, costly computing procedures for face detection (at each frame) can be avoided. According to an embodiment, a user itself can define an initial (reference) frame section. In general, the frame section 56 can be considered the area of the frame 66 which has to be tracked during measurement.

Figure 8:
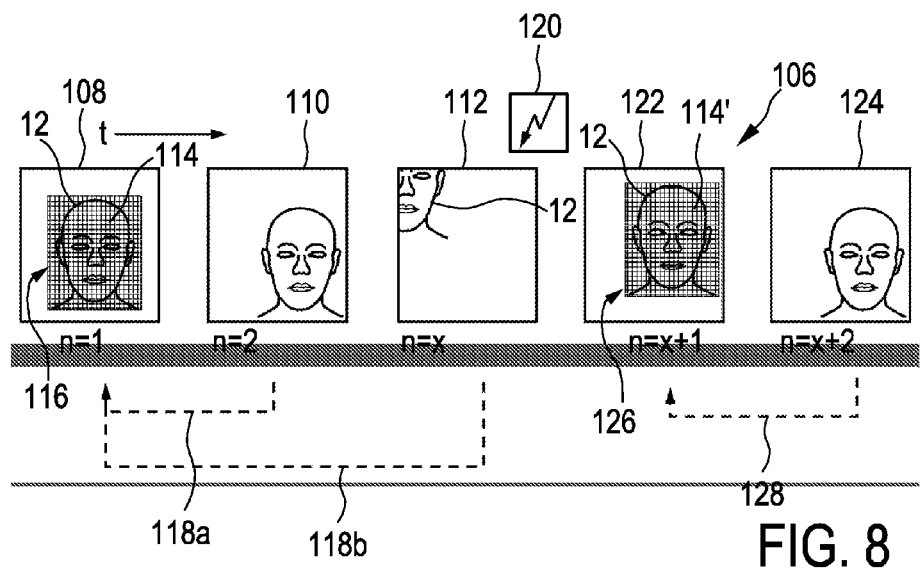
FIG. 8 shows a further sequence of frames representing a moving object.

FIG. 8 illustrates a further sequence 106 of frames 108, 110, 112, 122, 124 to be processed for motion compensation in a remote PPG environment.

According to an exemplary embodiment, the device 10 indeed can comprise a pattern detector 35 (refer to FIG. 1) which is configured for pattern detection, preferably for face detection. The frames 108, 110, 112, 122, 124 can be direct or immediate consecutive frames. Frame 108 serves as a reference frame. Applying a pattern detection algorithm, a detected pattern 114 representing a part of the object 12 to be observed can be selected and masked. Accordingly, a frame section 116 can be determined serving as a reference frame section to be tracked in subsequent frames 110, 112. Again, dimensional reduced derivative signal forms can be derived from the reference frame 108 and the subsequent frames 110, 112, refer to FIG. 5a and FIG. 5b. As mentioned above, each of the subsequent frames 110, 112 can be traced back to the reference frame 108 for comparing the respective derivative signal forms such that object shift can be detected, as indicated by dashed lines 118a, 118b. In frame 112 the object 12 is almost out of sight. Therefore, motion estimation can lead to a failure. Such a failure can be used as a trigger event as indicated by reference numeral 120. The trigger event 120 can re-initiate an initial stage of the motion compensation procedure. Basically, frame 122 can serve as a (new) reference frame. A pattern detection algorithm can be applied to reference frame 122. In this way, a certain pattern describing a region of the object 12 considered to be indicative of the vital signals to be extracted can be detected, refer to reference numeral 114'. Hence, a (new) reference frame section 126 can be determined which is to be tracked in subsequent frames 124. For further shift estimation and motion compensation each of the subsequent frames 124 can be compared with the (new) reference frame 122. In this way, the motion compensation procedure can be even more robust, since the algorithm can "refresh" upon certain trigger events 120. It should be understood that there exist several trigger events. As shown above, the object 12 positioned out of sight can cause the trigger event 120. Furthermore, an occluded object 12 can cause the trigger event 120.

Figure 9:
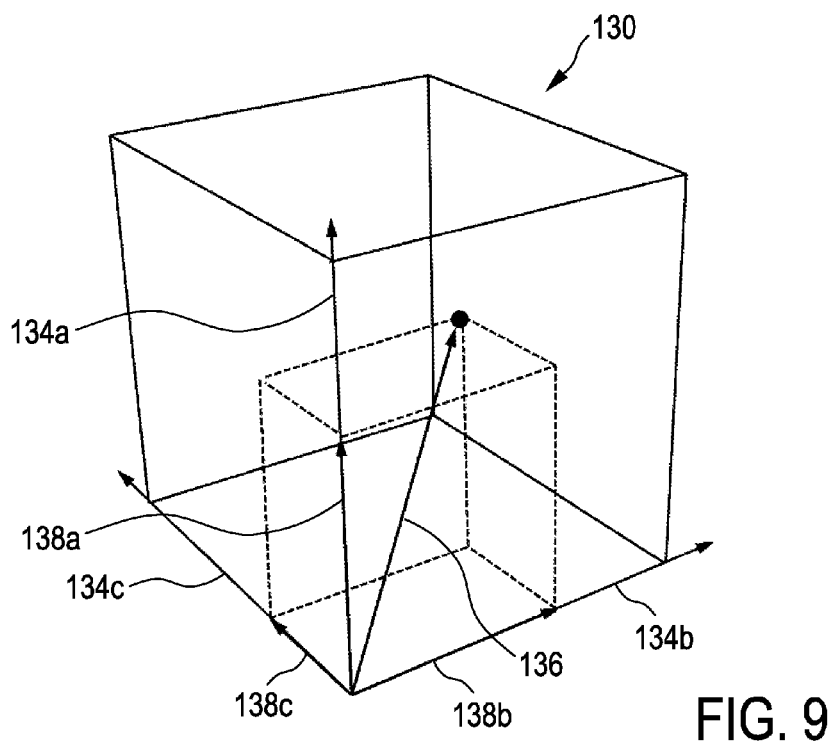
FIG. 9 shows an exemplary schematic illustration of a signal space comprising a characteristic signal.

FIG. 9 illustrates an exemplary signal space 130 comprising a characteristic signal 136. The signal space 130 may be composed of complementary channels 134a, 134b, 134c. For instance, the signal space 130 can represent an RGB signal space. Therefore, the complementary channels 134a, 134b, 134c may stand for respective R-, G- and B-channels. The characteristic signal 136 can be represented or embodied by a certain point (or: vector) in the signal space 130. The characteristic signal 136 can be composed of respective main components 138a, 138b, 138c each of which representing a certain value at the respective complementary channels 134a, 134b, 134c.

The characteristic signal 136 can be a representation of sub-entities of an (image) frame at a certain instant. For instance, the characteristic signal 136 can represent mean pixel values of the region of interest. In other words, for instance, when the region of interest mainly comprises skin pixels, the characteristic signal 136 basically represents a mean skin color the object 12 to be observed exhibits. Slight fluctuations of the skin color can cause slight fluctuations of the characteristic signal 136. These slight fluctuations can be interpreted as physiological information. The desired vital signals of interest can be extracted from the physiological information.

Figure 10A:
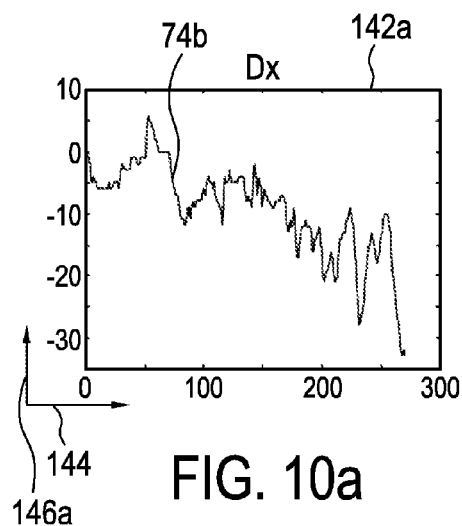
FIG. 10a, 10b depict two diagrams, each showing a directional motion component of an object motion.
Figure 10B:
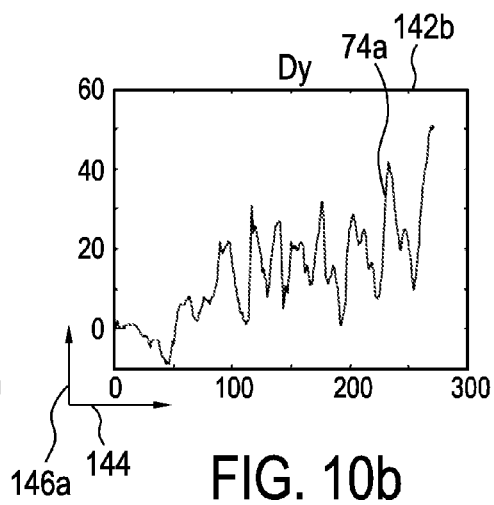
Figure 10C:
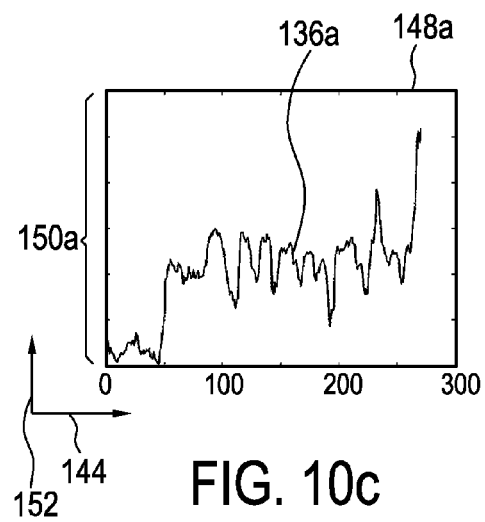
FIG. 10c, 10d depict two diagrams, each showing a characteristic signal in which physiological information is embedded from which a vital signal of interest can be derived.
Figure 10D:
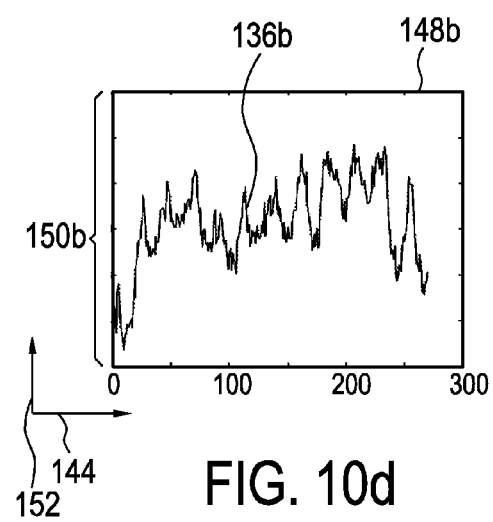

Referring to FIGS. 10a, 10b, 10c and 10d, an exemplary relationship between object motion and signal quality for remote PPG measurement can be highlighted. FIGS. 10a, 10b, 10c and 10d depict several diagrams. The diagrams 142a, 142b, 148a, 148b have been obtained through an exemplary remote PPG measurement procedure, wherein object motion with respect to the sensor means (e.g. camera) occurred. FIGS. 10a and 10b illustrate object motion over time in a first frame direction (dx) and a second frame direction (dy). FIG. 10c illustrates a strong influence of objection motion to a characteristic signal in an environment to which no motion compensation has been applied. By contrast, FIG. 10d is based on the same measurement but comprises a characteristic signal which has been obtained from a data stream to which exemplary motion compensation measures have been applied. All diagrams cover the same time period. In each diagram a time axis is denoted by an arrow 144. In each of the diagrams time is "counted" in numbers of processed frames.

The directional shift diagram 142a exemplarily illustrates a horizontal shift component 74b. The directional shift diagram 142b exemplarily illustrates a vertical shift component 74a. Taken in conjunction, an overall shift 74 can be composed of the shift components 74a, 74b, refer also to FIG. 5b. Both ordinates 146a, 146b in the directional shift diagrams 142a, 142b can comprise dimensionless reference positional information with respect to a starting position (dx=0; dy=0) at a start time (number of frames=0).

FIG. 10c illustrates a diagram 148a showing a characteristic signal 136a obtained from frame sections of frames to which no motion compensation measures have been applied. When comparing FIG. 10c with FIGS. 10a and 10b it becomes clear that high directional shift amplitudes can be reflected by strong amplitudes of the characteristic signal 136a in diagram 148a. For instance, a huge shift at about 270 frames leads to a huge amplitude of the characteristic signal 136a at the same time instant. The ordinate 152 of both diagrams 148a, 148b shown in FIGS. 10c and 10d may be directed to a dimensionless actual representation of a distinct characteristic (e.g. R/G ratio and such like) of the characteristic signals 136a, 136b. The characteristic signal 136b in diagram 148b is motion compensated according to an exemplary approach outlined above. The characteristic signal 136a in diagram 148a in FIG. 10c is clearly influenced by the object motion shown in diagrams 142a, 142b. Having applied motion compensation measures, motion induced distortion is no longer dominant in the characteristic signal 136b in diagram 148b. Curly brackets 150a, 150b illustrate a range which is covered in the ordinate direction in the respective diagrams 148a, 148b of FIGS. 10c and 10d. It should be noted that the range 150a encompassed by the diagram 148a of FIG. 10c is far more larger than the range 150b encompassed by the motion compensated diagram 148b in FIG. 10d. Hence, remaining signal characteristics (e.g. extreme values, reversal points and such like) of the characteristic signal 136b becoming apparent in diagram 148b are considered to be highly indicative of the desired vital signal embedded therein.

By contrast, the characteristic signal 136a of the uncompensated diagram of FIG. 10c does not allow such conclusions, since the desired vital signal is "hidden" behind disturbances due to object motion.

Figure 11:
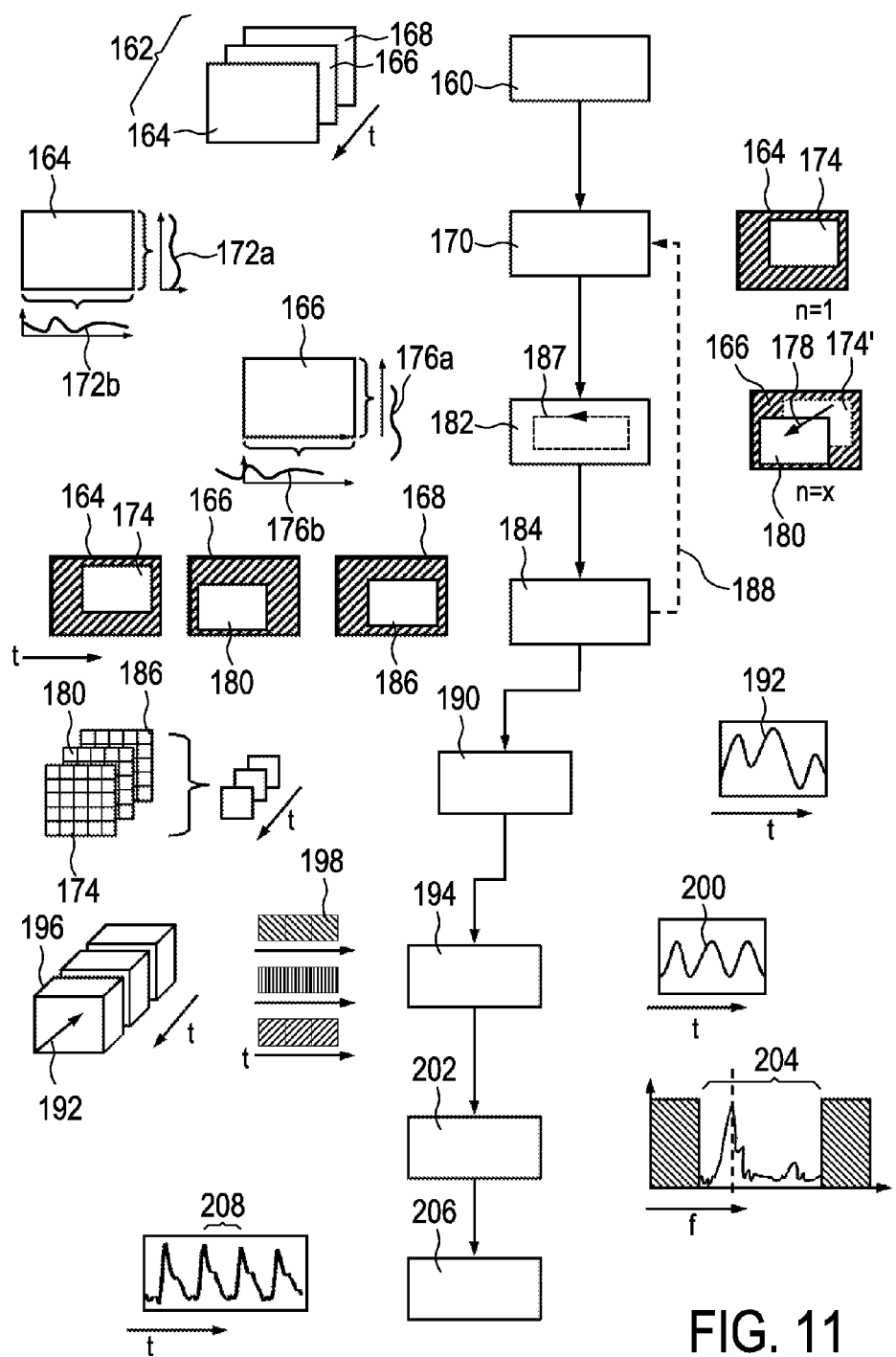
FIG. 11 shows an illustrative block diagram representing several steps of an embodiment of a method according to the invention.

Having demonstrated several alternative exemplary approaches covered by the invention, FIG. 11 is referred to, schematically illustrating a method for extracting information from characteristic signals.

Initially, in a step 160 an input data stream or a sequence 162 comprising several frames 164, 166, 168 is received. A time axis is indicated by an arrow t. The data stream can be delivered from the sensor means 22 or a data buffer or storage means. The data stream can be embodied, by way of example, by a sequence of image frames varying over time. The image frames can comprise RGB-based pixel data. The data stream comprises a representation of an object of interest.

In a subsequent step 170 a reference derivative signal form 172 comprising a first and a second reference derivative signal form component 172a, 172b can be derived from a reference frame 164. Furthermore, a reference frame section 174 can be determined in the reference frame 164. The reference frame section 174 is to be tracked during subsequent motion compensation measures. The reference frame section 174 can be determined manually or by applying a pattern detection (e.g. face detection) algorithm.

In another succeeding step 182 a subsequent frame 166 can be processed so as to derive a present derivative signal form 176 comprising a first and second derivative signal form component 176a, 176b. Through a comparison of the present derivative signal form 176 with the reference derivative signal form 172 a positional shift 178 can be estimated. Consequently, a frame section 180 can be determined in the frame 166 so as to track a region of interest to be observed. A reference position of the reference frame section 174 is indicated by reference numeral 174'.

It should be understood that step 182 can be repeated for each subsequent frame of the sequence of frames 162, refer to the dashed loop arrow 187. In this way, the frame section comprising the region of interest can be tracked over time, refer to the frame section 174 in frame 164, the frame section 180 in frame 166 and the frame section 186 in frame 168. A step 184 can comprise the respective determination of a sequence of frame sections. It is further remarked that each of the subsequent frames 166, 168 can be traced back to the reference frame 164 for motion detection and compensation. As indicated by a dashed line 188, the processing of a (new) reference frame can be initiated during the process based on the occurrence of trigger events.

Having determined a sequence of frame sections 174, 180, 186, the frame sections can be further processed in a subsequent step 190, wherein a characteristic signal 192 is extracted from the sequence of frame sections 174, 180, 186. For instance, the characteristic signal 192 can represent mean pixel values of the frame sections 174, 180, 186.

Another signal processing step 194 may follow in which instances of the characteristic signal 192 can be further processed. For instance, the characteristic signal 192 may contain color properties belonging to a signal space (or: color space) 196. Hence, the characteristic signal 192 can be split into respective main components 198 associated to signal space channels. Further signal processing may follow such that physiologic information 200 can be obtained. For instance, the physiologic information 200 can comprise information derived from slight fluctuations of the characteristic signal 192 which are considered highly indicative of desired vital signals to be obtained. A further signal processing step 202 may follow which can comprise, by way of example, signal filtering or signal weighting measures. In step 202 a defined frequency band 204 can be accentuated while adjacent frequency bands can be attenuated. Furthermore, frequency analysis can be applied to the processed data.

Eventually, in a further step 206 the processed physiological information signal 200 can be even further analyzed so as to extract the desired vital signal 208. It should be understood that a time-based representation and/or a frequency-based representation of the signal of interest 208 might be of interest.

By way of example, the present invention can be applied in the field of health care, e.g., unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases. Needless to say, in an embodiment of the method in accordance with the invention, several of the steps described here can be carried out in changed order, or even concurrently. Further, some of the steps could be skipped as well without departing from the scope of the invention. This applies in particular to several alternative signal processing steps.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for extracting information from remotely detected characteristic signals, comprising:
   an interface for receiving a data stream derivable from electromagnetic radiation emitted or reflected by an object, the data stream comprising a sequence of frames, at least some of the frames comprising a frame section representative of a region of interest attributable to the object, the region of interest exhibiting a continuous or discrete characteristic signal including physiological information, the physiological information being indicative of at least one at least partially periodic vital signal, the sequence of frames further comprising a disturbing signal portion at least partially indicative of undesired object motion, the disturbing signal portion adversely affecting the characteristic signal,
   a stabilizing processor comprising:
   a converter for deriving a reference derivative signal form from a reference frame of said sequence of frames, the reference derivative signal form being a dimensionally reduced representation of the reference frame of said sequence of frames and comprising at least a first reference signal component and a second reference signal component indicative of a reference positional information, and for deriving derivative signal forms respectively from at least some frames of said sequence of frames, each of the derivative signal forms being respectively a dimensionally reduced representation of each of the at least some frames of said sequence of frames and comprising at least a first signal component and a second signal component indicative of a positional information,
   a comparator for estimating a positional shift of a present derivative signal form relative to the reference derivative signal form, the positional shift being representative of an undesired object motion,
   a compensator for determining a present frame section under consideration of the estimated positional shift, the present frame section at least partially representing the region of interest, such that the region of interest can be tracked for at least partially compensating undesired object motion,
   an extractor for extracting the characteristic signal from the sequence of frames under consideration of a sequence of determined frame sections,
   wherein the characteristic signal is associated with a signal space representative of characteristics of the electromagnetic radiation,
   wherein the stabilizing processor is further configured for triggering the converter, based on a predetermined criterion, to update the reference derivative signal form by deriving another reference derivative signal form from another frame.

2. The device as claimed in claim 1, further comprising an analyzer for determining temporal variations of the characteristic signal, and for detecting the at least one at least partially periodic vital signal represented by the physiological information embedded in the characteristic signal.

3. The device as claimed in claim 1, wherein the converter is configured for agglomerating frame entities along a first direction and along a second direction of the least some frames of said sequence of frames so as to derive the derivative signal form, wherein the first signal component comprises a dimensional reduced mapping of frame lines and wherein the second signal component comprises a dimensional reduced mapping of frame columns.

4. The device as claimed in claim 1, wherein the at least one at least partially periodic vital signal is selected from the group consisting of heart rate, heartbeat, respiration rate, heart rate variability, Traube-Hering-Mayer waves, and oxygen saturation.

5. The device as claimed in claim 1, wherein the signal space is a color signal space comprising at least two complementary channels, the at least two complementary channels being related to defined spectral portions, and wherein the characteristic signal comprises at least two main components, each component being related to a respective complementary channel.

6. The device as claimed in claim 5, wherein the at least partially periodic vital signal is embedded in slight temporal fluctuations of at least one of the at least two main components of the characteristic signal.

7. The device as claimed in claim 1, wherein the stabilizing processor further comprises a pattern detector for determining a frame section at least partially representing the region of interest in at least one frame of said sequence of frames during an initial stage such that an initial frame section can be determined as a reference frame section.

8. The device as claimed in claim 1, wherein the stabilizing processor is further configured for correcting estimated positional shift values under consideration of present absolute shift estimates or temporal consistency of present shift estimates.

9. The device as claimed in claim 1, further comprising an integrated sensor capable of capturing the data stream comprising the sequence of frames.

10. The device as claimed in claim 1, further comprising a filter for selectively attenuating or enhancing components of the characteristic signal.

11. A method for extracting information from remotely detected characteristic signals, comprising:
   receiving a data stream derivable from electromagnetic radiation emitted or reflected by an object, the data stream comprising a sequence of frames, at least some of the frames comprising a frame section representative of a region of interest attributable to the object, the region of interest exhibiting a continuous or discrete characteristic signal including physiological information, the physiological information being indicative of at least one at least partially periodic vital signal, the sequence of frames further comprising a disturbing signal portion at least partially indicative of undesired object motion, the disturbing signal portion adversely affecting the characteristic signal, stabilizing the characteristic signal, comprising:

deriving a reference derivative signal form from a reference frame of said sequence of frames during an initial stage, the reference derivative signal form being a dimensionally reduced representation of the reference frame of said sequence of frames and comprising at least a first reference signal component and a second reference signal component indicative of a reference positional information, deriving derivative signal forms respectively from at least some frames of said sequence of frames, each of the derivative signal forms being respectively a dimensionally reduced representation of each of the at least some frames of said sequence of frames and comprising at least a first signal component and a second signal component indicative of a positional information, estimating a positional shift of a present derivative signal form relative to the reference derivative signal form, the positional shift being representative of an undesired object motion, determining a present frame section under consideration of the estimated positional shift, the present frame section at least partially representing the region of interest, such that the region of interest can be tracked for at least partially compensating undesired object motion, extracting the characteristic signal from the sequence of frames under consideration of a sequence of determined frame sections, wherein the characteristic signal is associated with a signal space representative of characteristics of the electromagnetic radiation, and triggering, based on a predetermined criterion, an update to the reference derivative signal form by deriving another reference derivative signal form from another frame.

12. A non-transient computer readable medium comprising a program code for causing a computer to:

receive a data stream derivable from electromagnetic radiation emitted or reflected by an object, the data stream comprising a sequence of frames, at least some of the frames comprising a frame section representative of a region of interest attributable to the object, the region of interest exhibiting a continuous or discrete characteristic signal including physiological information, the physiological information being indicative of at least one at least partially periodic vital signal, the sequence of frames further comprising a disturbing signal portion at least partially indicative of undesired object motion, the disturbing signal portion adversely affecting the characteristic signal;

stabilize the characteristic signal, comprising:

derive a reference derivative signal form from a reference frame of said sequence of frames, the reference derivative signal form being a dimensionally reduced representation of the reference frame of said sequence of frames and comprising at least a first reference signal component and a second reference signal component indicative of a reference positional information, derive derivative signal forms respectively from at least some frames of said sequence of frames, each of the derivative signal forms being respectively a dimensionally reduced representation of each of the at least some frames of said sequence of frames and comprising at least a first signal component and a second signal component indicative of a positional information;

estimate a positional shift of a present derivative signal form relative to the reference derivative signal form, the positional shift being representative of an undesired object motion;

determine a present frame section under consideration of the estimated positional shift, the present frame section at least partially representing the region of interest, such that the region of interest can be tracked for at least partially compensating undesired object motion;

extract the characteristic signal from the sequence of frames under consideration of a sequence of determined frame sections, wherein the characteristic signal is associated with a signal space representative of characteristics of the electromagnetic radiation; and trigger, based on a predetermined criterion, an update to the reference derivative signal form by deriving another reference derivative signal form from another frame.

* * * * *